(12) United States Patent
Bichler (10) Patent No.: US 10,617,547 B2
(45) Date of Patent: Apr. 14, 2020

(54) ORTHOPEDIC DEVICE FOR LIMITING THE MOVEMENT OF A JOINT DISPOSED BETWEEN A FIRST AND A SECOND BODY PORTION

(71) Applicant: Betterguards Technology GmbH, Berlin (DE)

(72) Inventor: Vinzenz Bichler, Berlin (DE)

(73) Assignee: Betterguards Technology GmbH, Berlin (DE)

( * ) Notice: Subject to any disclaimer, the term of this patent is extended or adjusted under 35 U.S.C. 154(b) by 252 days.

(21) Appl. No.: 14/404,003

(22) PCT Filed: May 24, 2013

(86) PCT No.: PCT/EP2013/060771
§ 371 (c)(1),
(2) Date: Nov. 25, 2014

(87) PCT Pub. No.: WO2013/174989
PCT Pub. Date: Nov. 28, 2013

(65) Prior Publication Data
US 2015/0173926 A1     Jun. 25, 2015

(30) Foreign Application Priority Data

May 25, 2012   (DE) .................. 10 2012 011 433

(51) Int. Cl.
*A61F 5/00*   (2006.01)
*A61F 5/01*   (2006.01)

(52) U.S. Cl.
CPC .......... *A61F 5/0104* (2013.01); *A61F 5/0111* (2013.01); *A61F 2005/0165* (2013.01); *A61F 2005/0169* (2013.01); *A61F 2210/00* (2013.01)

(58) Field of Classification Search
CPC .................. A61F 5/0104; A61F 5/0111; A61F 2005/0165; A61F 2005/0169; A61F 2210/00; A61F 5/019; A61F 5/0123; A61F 5/01; A61F 5/058; A61F 5/0585; A61F 5/05858; A61F 5/3723; A61F 5/373;
(Continued)

(56) References Cited

U.S. PATENT DOCUMENTS 547,412 A * 10/1895 McMahon ............... B62H 3/12
                                                        211/17
2,631,957 A *  3/1953 Francis, Jr. ............ B29C 70/08
                                                        156/178
(Continued)

OTHER PUBLICATIONS

Glenn, F. E. 2005. Chloroprene Polymers. Encyclopedia of Polymer Science and Technology.*

*Primary Examiner* — Keri J Nelson
*Assistant Examiner* — Adam Baker
(74) *Attorney, Agent, or Firm* — Ohlandt, Greeley, Ruggiero & Perle, L.L.P.

(57) ABSTRACT

An orthopedic device (1) for limiting the movement of a joint arranged between a first and a second region of a body is provided. The device includes at least one receptacle (2) that can be fixed on the first region of the body, and an extension element (3) that can be fixed on the second region of the body and is movable relative to the receptacle (2), wherein a volume filled with a dilatant fluid (4) is provided between the receptacle (2) and the extension element (3).

20 Claims, 4 Drawing Sheets

(58) Field of Classification Search
CPC ...... A61F 2005/0146; A61F 2005/0148; A61F 2005/0151; A61F 2005/0153; A61F 2005/0155; F16F 13/09; F16F 13/08; F16F 1/3605; F16F 7/12; F16F 9/006; F16F 9/30; F16F 9/512; F16F 9/53; F16F 2236/06; F16F 2236/103; A41F 1/00; A42B 3/14; A42B 3/08; Y10T 24/34; Y10T 24/16; Y10T 428/139; A61H 1/0274; A61H 1/0277
USPC ................ 602/61, 62, 63, 65, 66, 27, 28, 29
See application file for complete search history.

(56) References Cited

U.S. PATENT DOCUMENTS

| | | | |
|---|---|---|---|
| 3,799,159 A * | 3/1974 | Scott | A61F 2/64 602/16 |
| 4,237,873 A * | 12/1980 | Terry | A61F 5/013 602/20 |
| 4,471,538 A | 9/1984 | Pomeranz et al. | |
| 4,936,295 A * | 6/1990 | Crane | A61F 5/0111 36/89 |
| 5,352,190 A * | 10/1994 | Fischer | A61F 5/0123 602/20 |
| 5,712,011 A * | 1/1998 | McMahon | A41F 1/00 2/338 |
| 6,689,074 B2 * | 2/2004 | Seto | A61F 2/54 601/33 |
| 7,342,049 B2 * | 3/2008 | Minemura | C08L 83/04 516/33 |
| 7,402,147 B1 | 7/2008 | Allen | |
| 2003/0073941 A1 * | 4/2003 | Betz | A61F 5/0118 602/5 |
| 2006/0173391 A1 * | 8/2006 | Bodenschatz | A61F 5/058 602/12 |
| 2007/0107778 A1 | 5/2007 | Bettin et al. | |
| 2010/0000551 A1 * | 1/2010 | Li | A61F 5/566 128/848 |
| 2012/0089065 A1 | 4/2012 | Pflaster et al. | |
| 2012/0186003 A1 * | 7/2012 | Heger | A41D 13/015 2/412 |

\* cited by examiner

ORTHOPEDIC DEVICE FOR LIMITING THE MOVEMENT OF A JOINT DISPOSED BETWEEN A FIRST AND A SECOND BODY PORTION

TECHNICAL FIELD

The present invention relates to an orthopedic device for limiting the movement of a joint disposed between a first and a second body portion, comprising at least a receptacle fixable to the first body portion and a pull-out body fixable to the second body portion and movable relatively to the receptacle.

STATE OF THE ART

Damages in the area of joints involved in the cycle of movement belong to one of the most important accident black spots. In particular, emphasis is put on "accidents relating to tripping, slipping and falling" (TSF-accidents), which most frequently occur as accidents relating to commuting, working and sports. Separately or in combination these accidents can lead to significant injuries. Especially larger joints as the upper and lower ankle joint (*articulatio talocuralis* and *articulatio talotarsalis*), the wrist (*articulatio manus*) and the knee joint (*articulatio* genus) are mainly affected. Thereby, in this area a tendency to injury can also be registered in terms of sports medicine.

The TSF-accidents often lead to a violent strain of the support structure of the joint (joint capsule, ligaments, tendons, bones) beyond the physiological maximum possible angle. This strain is also known under the term distorsion or sprain. As in terms of the ankle joint and the wrist this often occurs in the direction of supination, in this case it is spoken of a so-called supination trauma. This is a synonym for an injury, wherein a supination of the foot that was made beyond the physiological room for maneuver together with a plantar flexion leads to a damage of the lateral bone structures and the lateral collateral ligaments apparatus. Initially supination traumas are revealed in violent pain that mostly are linked to a swelling of the appendage and to the migration of a hematoma (in the case of ruptured ligaments). If such accompanying symptoms are not recognized and medical care is not sufficiently provided, remote damages such as a chronic instability of the joints or joint arthrosis may occur.

A very important factor for the positive healing process of a supination trauma is the stabilization of the joints of the patient for the prevention of injuries or during care before or after an operation. Thereby, the stabilization of the joints is normally achieved through tape strappings, orthoses for the assurance of function, orthoses of stabilization, bandages and/or stable shoes with a shaft with variable height and optional reinforcement elements.

In general and in this application, orthosis can be understood as a function assuring, body enclosing or body adjacent aid that in terms of its physical/mechanical performance constructively stabilizes, immobilizes, mobilizes, relieves, corrects, retains, fixes, redrills and/or replaces failed body functions.

Furthermore, orthoses may consist of body part enclosing shafts that are manufactured as closed or windowed frame shafts. Thereby, the shaft systems are fixed to the body by means of fastenings (such as Velcro). Further, the shaft systems of joint comprehensive orthosis can be interconnected in accordance with the functional requirements by means of unilateral or bilateral splint systems. Furthermore, it can be distinguished between static orthoses for fixing, correcting and supporting one or more joints and dynamic orthoses for applying a constant force to a movable body part.

For example, the DE 10 2005 002 834 B4 shows an orthopedic apparatus for stabilizing, relieving and guiding the foot and the toes in case of paralysis of the dorsal tensors of foot and toes. Thereby the apparatus comprises a device for holding on to the lower leg, on which a complete or in sections flexible splint is attachable reversibly or irreversibly, which points forward and into the direction of the foot.

The U.S. Pat. No. 5,472,412 shows an articulated knee brace including a pair of arms pivotally connected by corresponding pivot pins and gear segments supported by a set of hub plates having wholes for receiving adjustable stop pins. The arms are attached by flexible and releasable bands to a person's limb or opposite sides of a joint, and one of the arms carries an adjustable hydraulic control unit, which comprises a set of rotatable valves controlling the flow of hydraulic fluid through the valves and between two piston chambers disposed in the control unit. Thereby, a resistance to flection and extension of the brace and limb can be adjusted manually.

The term bandages can be understood in general and in the present application as body part enclosing or body part adjacent tailored aids with a compressing and/or function assuring effect. As a rule, soft, elastic textile materials are used.

Bandages can fulfill the function of saving joints and bones from overstressing or treating acute or chronic tissue disorders.

The EP 0 600 218 B1 shows a bandage for the knee joint of elastic bandage cloth in tubular form with a front bandage portion and a rear bandage portion and with at least one inserted, longitudinally proceeding spring bar.

In general and in the present application under the term tape dressing a dressing for stabilizing, supporting and holding of extremities, protection from further injuries, reduction of unintended joint movements and supporting of the healing process can be understood. Tape dressings are used for prophylaxis, first aid, therapy and rehabilitation.

As a rule, orthoses comprise a complex method of construction, which mostly is accompanied by a complicated attachment to the body or a complicated adjustment. Moreover, orthoses can require a high material inventory, which not rarely leads to a bulky method of construction. The fact that the resistance of the orthoses, as a rule, has to be set manually, is to be seen as a further disadvantage.

Bandages in general show a limited supporting effect. Furthermore, wearing bandages is often linked to the formation of bruises.

A disadvantage of tape dressings is that their stabilization effect does not last long. As a rule, it is only at 50% after the first 10 minutes.

PRESENTATION OF THE INVENTION

Starting from the prior art it is an object of the present invention to provide an orthopedic device for limiting the movement of a joint disposed between a first and a second body portion, comprising at least a receptacle fixable to the first body portion and a pull-out body fixable to the second body portion and movable relative to the receptacle, which improves the limitation of the movement.

This object is solved by means of a device with the features of claim 1. Advantageous embodiments can be taken from the dependent claims.

Accordingly, an orthopedic device for limiting the movement of a joint disposed between a first and a second body portion is given, comprising at least a receptacle fixable to the first body portion and a pull-out body fixable to the second body portion and movable relative to the receptacle. According to the invention a volume filled with shear thickening fluid is provided between the receptacle and the pull-out body.

In the case that a high force or a jerking movement is applied to the joint, the shear thickening fluid can oppose by limiting the movements of the pull-out body relative to the receptacle. However, the shear thickening fluid allows an almost unlimited movement of the pull-out body relative to the receptacle in case of slow, weak joint movements.

Thus, undesirable movements can be prevented. Fast or jerking movements, which can have a negative effect on the healing process, can be avoided for example. Additionally, by limiting the movement overstretching or straining of the particular joint can also be prevented. Furthermore, the orthopedic device can enable an extension of the reaction time of the muscles.

Thus, the joint or the corresponding body portion can be supported and fixated depending on the acting force.

Due to the adaptive limitation of movement there is a broad application scope for the orthopedic device. Hence, the orthopedic device can be attached to orthoses and protectors as well as bandages.

Furthermore, fields like sports equipment, prostheses, protective clothing and the like come into consideration. In particular, the orthopedic device can also be integrated into shoes, fitness bandages and/or working aids, such as gloves.

Thus, the orthopedic device can be used for therapeutic purposes as well as prophylactic purposes. In the context of a therapeutic use, the device can be carried out such that partial loads of the corresponding body portion are allowed, which can have a positive effect on the healing process.

For an adaptive limitation of movement shear thickening materials such as copolymer dispersions or fluids are used, which show a higher viscosity when high shear forces and an accompanying high shear rate occur. The bigger the applied shear is, the more viscose or thicker is the behavior of the fluid. Accordingly, shear strengthening or shear thickening properties are attributed to shear thickening fluids.

In general and in particular in the present application shear thickening fluids are to be understood as copolymer dispersions, such as shown in DE 30 25 562 A1, DE 34 33 085 A1 and DE 39 17 456 A1. The dispersions for example are composed of emulsion copolymers and metallic salts. The emulsion copolymers for example can be polymerized of 1-10%-by weight monoolefinic unsaturated monocarboxylic acid and/or dicarboxylic acid, such as acrylic acid, metacrylic acid, maleic acid and/or fumaric acid, 99-90%-by weight other olefinic unsaturated monomers, such as styrene, C1-C6-alcylacrylates, such as methylmetacrylate, and 5-30%-by weight of carboxylic acid allyl ester-monomers with two or more copolymerizable double bonds, such as diallyl phthalate.

As metallic salts 0.1 to 30%-by weight referring to the copolymerisate of metal oxides, metal hydroxides, metal halides, metal carbonates, metal hydrogen sulfates, metal sulfates and/or metal phosphates are added.

Furthermore, the shear thickening liquids comprise thinning agents, such as alcohols, glycols, diglycols and triglycols, formamides and/or water. For a detailed composition of the shear thickening fluids it is referred to DE 30 25 562 A1 and DE 39 17 456 A1.

Shear thickening fluids can also be simple dispersions, which show shear thickening properties up from a particular solid content.

In a further preferred embodiment the used shear thickening fluid can also comprise a dispersion of ethylenglycol (for example with a molar mass of 62 g/mol), silicon dioxide, preferably silica gel with a particle size of 5 to 1000 nm and surfaces of 30 to 250 $m^2$/g, with a solid content of 10-80%-by weight and appropriate stabilizers.

In a preferred embodiment the pull-out body is linearly movable disposed in the receptacle. Thereby, a directed assurance of function, fixation, correction and/or support of a joint is enabled.

In a preferred embodiment the volume filled with shear thickening fluid is defined by a gap between the inner surface of the receptacle and an outer surface of the pull-out body. Thereby the part of the pull-out body, which is located in the inside of the receptacle, is completely surrounded by the shear thickening fluid and can interact with the shear thickening fluid depending on the size of the forces acting on the pull-out body. When a defined small force is applied, the pull-out body can be moved in the shear thickening fluid almost unrestrictedly. When a high force is applied, which results in a strong or abrupt tension on the pull-out body the critical shear rate in the shear thickening fluid is exceeded. Depending on the used fluid this results in an increase of the tensile stress by the factor 100 to the factor 1000. The increase of the tensile stress has a linking effect on the shear thickening fluid, whereby the pull-out body, on which a high force is applied, is held in the shear thickening fluid and, thus, undergoes no or only a reduced movement.

In a further preferred embodiment the gap comprises a clearance of 0.1 to 100 mm, preferably 0.1 to 50 mm, more preferably 0.1 to 15 mm and even more preferably 0.1 to 5 mm. Depending on the size of the clearance the retention force can be adjusted application-orientated. Hence, depending on the application next to the solid contents, which can be provided by additives such as stabilizers, dispersion agents and/or the like, the desired shear thickening/shear strengthening can also be modified or adjusted by means of the clearance.

The dimension of the clearance also affects the overall height of the orthopedic device. Thus, by choosing a small clearance in conjunction with a flat receptacle and with an accompanying flat pull-out body all in all a flat orthopedic device can be achieved. Those particular flat orthopedic devices prove to be extremely user friendly as they disturb the user during wearing only little due to their compact foot print. Hence, for example, clothes can be put-on or taken-off more easily over such flat orthopedic devices. Furthermore, a flat device can more easily be integrated into clothes, such as foot wear.

In a further embodiment the gap comprises a first clearance between the inner surface of the receptacle and a first and a second surface of the pull-out body, and a second clearance between the inner surface of the receptacle and lateral surfaces of the pull-out body. Thereby, the first clearance differs from the second clearance. Thereby, between the inner surface of the receptacle and the lateral surfaces of the pull-out body, for example, a smaller clearance can be chosen, so that the lateral surfaces of the pull-out body serve as the lateral guiding of the pull-out body in the receptacle.

The interaction of the shear thickening fluid with the pull-out body predominantly takes place between the shear thickening fluid and the first and second surfaces of the pull-out body. Accordingly, the interaction between the shear thickening fluid and the pull-out body can be defined by changing the clearance between the inner surface of the receptacle and the first and second surfaces of the pull-out body.

In a further preferred embodiment the orthopedic device comprises means to reset the pull-out body into a starting position in the receptacle. Thereby, the orthopedic device can lead back the concerned joint into a resting position, as far as no forces are applied to the joint. Accordingly, the starting position of the pull-out body in the receptacle should be chosen in such a way that if the orthopedic device is in the starting position, the concerned joint is in the preferred resting position.

Moreover, by means of the reset means the adoption of the resting position preferred by the user can also be supported.

If the pull-out body again is transferred into the starting position by the reset means, the entire stroke length for the adaptive limitation of movement of the concerned joint is available to the orthopedic device and in particular to the pull-out body.

In a further preferred embodiment the reset means comprises an elastic synthetic material, a spring, two permanent magnets and/or a sealing between the receptacle and the pull-out body. By using an elastic synthetic material the tension force of this elastic synthetic material can be used in order to reset the pull-out body to the starting position. An elastic synthetic material, for example in form of a rubber band, is a simple, cost-effective reset means. When using a spring as means to reset the pull-out body into the starting position, the reset is determined by the elasticity of the spring. The use of two permanent magnets as reset means of the pull-out body, wherein one permanent magnet is disposed on the pull-out body and another permanent magnet is disposed on the receptacle, has the advantage that the resets of the pull-out body into the starting position in the receptacle can be achieved contactless. Thus, a tight connection between the pull-out body and the receptacle is not required.

By using the sealing as reset means of the pull-out body components or production costs can be saved compared to other solutions. Moreover, a sealing, which as a rule at its ends is circumferentially connected to the receptacle and the pull-out body, has an equally distributed transfer of the reset force onto the pull-out body.

In a further embodiment the surfaces of the pull-out body (3) and/or of the receptacle (2), which are in contact with the shear thickening fluid (4) and run perpendicular to the normal of the pull-out direction, comprise a structure. Thereby, the surfaces of the pull-out body or of the receptacle communicating with the shear thickening fluid are increased. Larger surfaces of the pull-out body or the receptacle lead to a larger interaction of these surfaces with the shear thickening fluid. Accordingly, by means of the structured surfaces compared to unstructured surfaces with the same dimensions higher shear forces and, thus, an earlier starting jump in dilatancy, at which a clear increase of the viscosity can be recorded, can be achieved.

For the viscosity of the shear thickening fluid this means that by means of the structure of the surface the same viscosity is possible at a smaller clearance. Thereby, in turn available space can be saved, whereby the orthopedic device all in all becomes more user friendly.

In a further preferred embodiment the structure of the surfaces comprise shapings, fins, grooves and/or nubs or consists of a rough surface. Thereby, the effect of the structure described above can be achieved. Accordingly, the surfaces in communication with the shear thickening fluid can be enlarged by means of shapings, fins, grooves and/or nubs on the pull-out body and/or the receptacle. Larger surfaces of the pull-out body or the receptacle can provide larger interactions of these surfaces with the shear thickening fluid, whereby higher shear forces and, thus, an earlier starting jump in dilatancy may arise.

In a further embodiment the receptacle comprises an opening, out of which the pull-out body protrudes. Thereby, a holding device or the portion of a holding device, which have a body portion enclosing, force absorbing, force transmissing and fixating function, can be mounted on the protruding portion of the pull-out body. Thereby, the holding device or the part of the holding device is disposed at a body portion, which borders on the joint that is to be adaptively limited in its movement.

In a further preferred embodiment the receptacle has a sealing in order to seal the movement of the pull-out body. Thereby, it can be assured that the shear thickening fluid is always kept in the inside of the receptacle when retracting and extending the pull-out body. Accordingly, the sealing provides that no residues of the shear thickening fluid remain on the surface of the portion of the pull-out body, which is located outside of the receptacle. Thus, it can be assured that the shear thickening fluid does not contaminate the immediate vicinity of the orthopedic device and in particular that the user does not get into contact with the shear thickening fluid. Thereby, for example, the sealing can be formed as a circumferential sealing lip.

Furthermore, the sealing prevents that the amount of shear thickening fluid situated in the receptacle is being reduced by the movement of the pull-out body. Thus, the shear thickening fluid is not used-up by the use of the orthopedic device and does not or more rarely has to be refilled.

In a further preferred embodiment the sealing at a first end is connected to the receptacle and at a second end is connected to the pull-out body, wherein the sealing is movable like a bellows. Thus, the sealing is able to follow the movements of the pull-out body. Accordingly, the bellows unfolds between the first and the second end of the sealing, when the pull-out body is moved out of the receptacle. However, if the pull-out body is moved into the receptacle, a bellows-type folding of the sealing is achieved.

Neither the second end of the sealing nor the first end of the sealing has to be sealed against a movable body. That means, no circumferential sealing lip is required to which a body moves relatively. Between the two ends of the sealing and the receptacle or the pull-out body there is a force fit or friction fit connection, rather.

In a further preferred embodiment the receptacle and/or the pull-out body are made of synthetic material, preferably of thermoplastic synthetic material, more preferably of polypropylene, polyethylene and/or polyurethane. The use of synthetic material provides the strength and stiffness required in the range of application of the orthopedic device at a low weight at the same time. A low weight of the orthopedic device particularly can have advantageous effects for the wearing comfort. Furthermore, synthetic material has a high biocompatibility, which can be advantageous especially during constant or longer lasting skin contact. Further, the used synthetic materials also meet the medical hygiene requirements.

Furthermore, the use of synthetic material also enables the production by means of two component injection molding.

Thereby, for example, a sealing can be integrated into the pull-out body already at the production.

In a preferred embodiment the pull-out body comprises reinforcement fibers, preferably natural fibers, aramid fibers, glass fibers, carbon fibers or other synthetic fibers. Thereby, the movement of the orthopedic device can be increased. Hence, the portions of the fibers of the pull-out body, which protrude out of the receptacle, can extend in almost any direction. Thus, an orthopedic device with a fibrous pull-out body is suited especially for body portions that require a high freedom of movement.

Moreover, by means of a fibrous pull-out body available space as well as weight can be saved. As the fibers can only be subjected to tension, a reset means of the pull-out body is required as a rule.

In a further embodiment the receptacle and/or the pull-out body comprise a holding device, which is mountable on a body portion. Thereby, a flow of forces can be led via the orthopedic device from one body portion to another body portion, wherein a joint located between the two of the body portions can be relieved. Due to the mentioned properties of the orthopedic device the relative movement of the body portions to each other and, thus, the movement of the joint located between the body portions, can be adaptively limited.

Furthermore, by mounting of the holding device a starting position of the orthopedic device on the body of the user can be determined.

BRIEF DESCRIPTION OF THE DRAWINGS

Preferred further embodiments and aspects of the present invention are explained further by the following description of the Figures.

DETAILED DESCRIPTION OF PREFERRED EMBODIMENTS

Hereafter preferred embodiments are described by means of the Figures. Thereby, the same elements, similar elements or elements with the same effect are indicated by identical reference signs. To avoid redundancies the following description partially goes without a repeated description of these elements.

Figure 1:
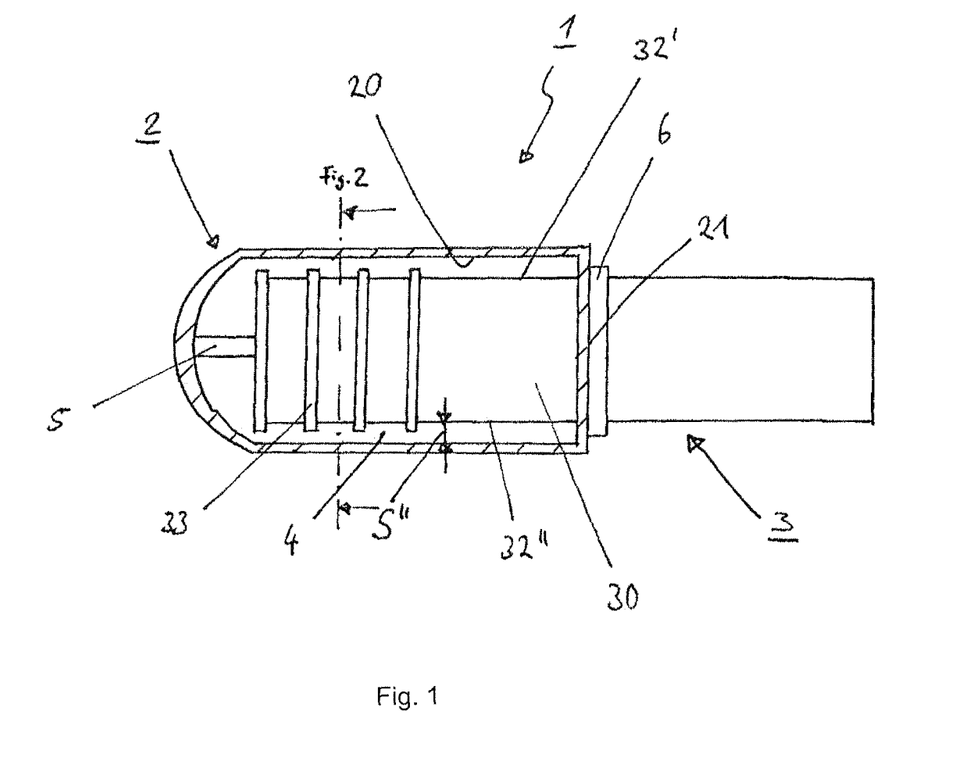
FIG. 1 shows a schematic top view of a section through the orthopedic device.

FIG. 1 shows schematically an orthopedic device 1 for limiting the movement of a joint disposed between a first and a second body portion. Thereby, the device 1 comprises a receptacle 2, which can be fixed to the first body portion. Furthermore, FIG. 1 shows a pull-out body 3, which can be fixed to the second body portion and extends partly into the inside of the receptacle 2. The volume resulting between the pull-out body 3 and the inner surface 20 of the receptacle 2 is filled with a shear thickening fluid 4. By means of applying force to the orthopedic device an interaction between the shear thickening fluid 4 and the surface of the pull-out body 3 can be achieved, whereby the movement of the pull-out body 3 relative to the receptacle 2 can be influenced.

Figure 3:
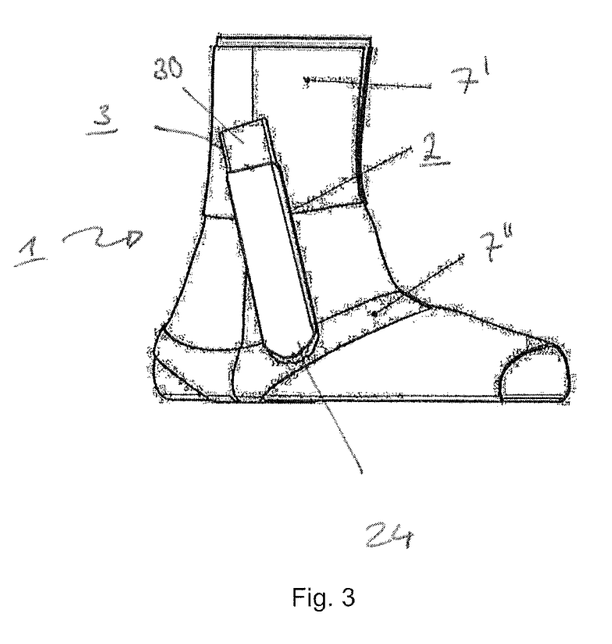
FIG. 3 shows schematically the orthopedic device of FIG. 1 in an arrangement for the adaptive limitation of movement of an ankle joint.

The orthopedic device 1 for the adaptive limitation of movement of a joint disposed between two body portions shown in FIG. 1 comprises the receptacle 2, which is mounted on a holding device 7', 7" for example shown in FIG. 3. By means of the holding device 7', 7" the receptacle 2 can be fixed on a body portion of a user.

The receptacle 2 is dimensioned such that it can accommodate a pull-out body 3 in its inside. For accommodating the pull-out body 3 there is an opening 21 at the end of the receptacle 2.

The receptacle 2 is made out of synthetic material, which in particular is impermeable to fluids. Preferably a thermoplastic synthetic material is used, wherein the thermoplastic synthetic material can be polypropylene, polyethylene and/or polyurethane.

FIG. 1 further shows the pull-out body 3, which is partially located in the inside of the receptacle 2. At the end of the portion of the pull-out body 3, which protrudes out of the receptacle 2, the pull-out body 3 can be connected to a body portion of a user by means of a holding device 7', 7" as shown, for example, in FIG. 3.

The pull-out body 3 is held linearly movable in the receptacle 2 in a rail guidance (not shown), for example. Thereby, the pull-out body 3 can be retracted into the receptacle 2 or extended out of the receptacle 2 through the opening 21 of the receptacle 2.

The pull-out body 3 has a cuboid shape and has a first surface 30, a second surface 31 (not shown in FIG. 1) and lateral surfaces 32', 32". Between the inner surface 20 of the receptacle 2 and the first surface 30, the second surface 31 and the two lateral surfaces 32', 32" of the pull-out body 3 there is a gap with a clearance S. This clearance S results from the difference in volume of the inner volume of the receptacle and the displaced volume of the portion of the pull-out body, which is disposed in the inside of the receptacle.

Moreover, the volume between the receptacle 2 and the pull-out body 3 is filled with a shear thickening fluid 4. When the pull-out body 3 is moved into the receptacle 2 or out of the receptacle 2, the movement of the pull-out body 3 is influenced by the properties of the shear thickening fluid 4. Accordingly, if the orthopedic device 1 is retracted or extended under a low applied force, the shear thickening fluid 4 allows that the pull-out body 3 moves within the shear thickening fluid 4. The bigger the forces acting on the orthopedic device 1 are, which move the receptacle 2 and the pull-out body 3 into each other or apart from each other, the bigger are the shear forces acting between the pull-out body 3 and the shear thickening fluid 4. With the increase of the shear forces also the viscosity of the shear thickening fluid increases. Thereby, the shear thickening fluid for example shows a jump in dilatancy, at which an obvious increase of the viscosity can be recorded. Thus, the receptacle 2 and the pull-out body 3 of the orthopedic device 1 can not or only slightly be moved towards each other when a viscosity in the shear thickening fluid 4 is high, especially above the jump in dilatancy.

FIG. 1 further shows that the pull-out body 3 has a structure 33. The structure 33 provides a bigger surface of the pull-out body 3. In FIG. 1 the structure 33 is formed in form of grooves. The structured surfaces are surfaces, which are disposed vertically to the normal of the pull-out direction. Alternatively, also fins, nubs or the like are possible. Due to the increase of the surface of the portion of the pull-out body 3, which is in contact with the shear thickening fluid 4, the properties of the orthopedic device can be changed to that effect that at comparatively low shear forces there is already a high increase of viscosity of the shear thickening fluid 4. Thereby, for example, a jump in dilatancy can be shifted to that effect that it occurs earlier, i.e. at lower shear forces as with a pull-out body without a structure.

FIG. 1 further shows reset means 5 of the pull-out body 3 in a starting position in the receptacle 2. Depending on the joint to be supported the reset means 5 can be required to lead back the joint into a resting position after it had been deflected. Thereby, the reset means 5 is chosen such that the joint experiences a gentle deflection or that the pull-out body 3 is guided that slowly through the shear thickening fluid 4 so that no relevant increase of the viscosity in the shear thickening fluid 4 evokes.

The reset means 5 shown in FIG. 1 is an elastic synthetic material in the form of a rubber band with the properties described above. Alternatively the reset means can also be formed by a spring, by a pair of permanent magnets, wherein the one permanent magnet is disposed at the end of the receptacle 2 and the other permanent magnet is disposed at the opposing end of the pull-out body 3, or by an elastic sealing. Moreover, the reset of the pull-out body 3 can also be carried out by negative pressure prevailing in the receptacle 2. The negative pressure arises by pulling-out the pull-out body 3 by means of an appropriate sealing.

Furthermore, a sealing 6 can be taken from FIG. 1, which his located on the opening 21 of the receptacle 2 and seals the inside of the receptacle 2 against the outer vicinity. the sealing 6 surrounds the opening 21 of the receptacle 2 or the first surface 30, the second surface 31 and the lateral surfaces 32', 32" of the pull-out body 3. Thereby, the pull-out body 3 can be moved relatively to the sealing 6. A circumferential sealing lip of the sealing 6 prevents that shear thickening fluid 4 escapes from the inside of the receptacle 2 through the opening 21.

Alternatively, the sealing 6 can also have the form of a bellows. Thereby, a first end of the sealing bellows is connected tight with the receptacle 2 and a second end of the sealing bellows is connected tight with the pull-out body 3. If the pull-out body 3 is moved out of the receptacle 2, the distance between the first end of the sealing bellows and the second end of the sealing bellows increases. Accordingly, the sealing bellows follows the movement of the orthopedic device 1 or the pull-out body 3.

Moreover, a sealing bellows additionally can take over the function of the reset means 5. In this case the bellows body of the sealing has an elasticity that allows to take-up a resting position again after deflection of the orthopedic device 1 by means of the first end of the bellows sealing and the second end of the bellows sealing again approaching each other. As sealing material, for example, elastic rubbers or polymers are used.

Also the pull-out body 3 is made out of synthetic material. Thereby, preferably thermoplastic synthetic materials, such as polypropylene, polyethylene or polyurethane are used.

Figure 2:
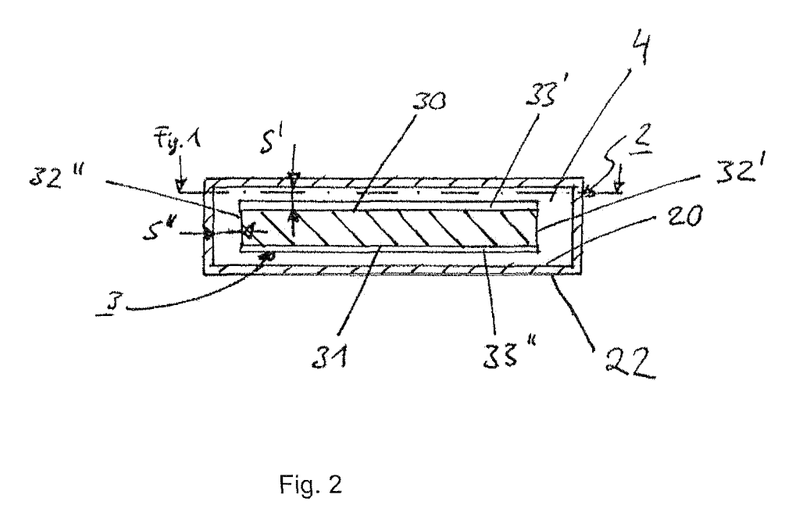
FIG. 2 shows a schematic cross-sectional view of the orthopedic device of FIG. 1.

FIG. 2 shows a sectional view of the orthopedic device 1 of FIG. 1 rotated by 90°. Thereby, FIG. 2 shows the arrangement of the pull-out body 3 in the inside of the receptacle 2. The first surface 30 and the second surface 31 of the pull-out body 3 each are spaced from the inner surface 20 of the receptacle 2 of the clearance S'. The lateral surfaces 32', 32" of the pull-out body 3 are spaced from the inner surface 20 of the receptacle 2 by the clearance S". Thereby, the clearances S' and S" differ from each other.

FIG. 3 shows the orthopedic device of FIG. 1 in an arrangement for the adaptive limitation of movement of an ankle joint. Thereby, the orthopedic device 1 is fixed to body portions, which border the ankle joint, via the holding device 7',7".

The end of the portion of the pull-out body 3, which protrudes out of the receptacle 2, is attached to the holding device 7'.

The outer surface 22 of the receptacle 2 is attached to the holding device 7" in the area of a closed end 24.

The holding device 7' and 7" is mounted to the body of the user such that the effected joint is located in between.

The pull-out body 3 or the receptacle 2 are adhered onto the holding device 7' or 7", respectively. Alternatively, the pull-out body 3 or the receptacle 2 can also be sewed, screwed, tied or fastened via Velcro to the holding device 7', 7". Furthermore, also the connection by means of a ball joint is possible.

Figure 4:
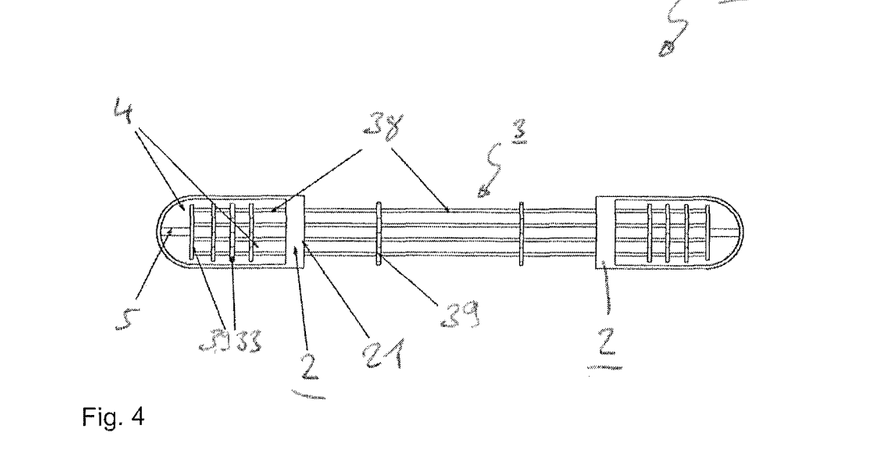
FIG. 4 shows schematically an orthopedic device with two receptacles.

FIG. 4 schematically shows an orthopedic device 1, wherein both ends of the pull-out body 3 are each held in a receptacle 2. The assembling of the receptacle 2 is similar to the receptacle of FIG. 1.

Further, the pull-out body 3 consists of single pull-out rods 38, which are held together by means of cross members 39. Thereby, in the inside of the receptacle 2 the shear thickening fluid 4 can also flow into the space between the pull-out rods 38. The pull-out rods are made of thermoplastic synthetic material, more preferably out of polypropylene, polyethylene and/or polyurethane.

Alternatively, instead of the pull-out rods 38 also fiber strands made out of reinforcement fibers can be used. Also the fiber strands are hold together by means of cross members 39. As the fibers can only be subjected to tension in such an embodiment, the reset means 5 of the pull-out body 3 has a distinctive role, as the pull-out body 3 or the fiber strands without the reset means 5 are not able to return to a starting position after a deflection by means of forces applied to the orthopedic device 1. Natural fibers, aramid fibers, glass fibers, carbon fibers or other synthetic fibers can be used as fibers.

The receptacles 2 shown in FIG. 4 have several openings 21, through each of which a pull-out rod is led. Thereby, in every opening 21 a sealing 6 is disposed, which prevents that shear thickening fluid 4 escapes from the inside of the receptacles 2 during movement of the pull-out rods 38.

Figure 5:
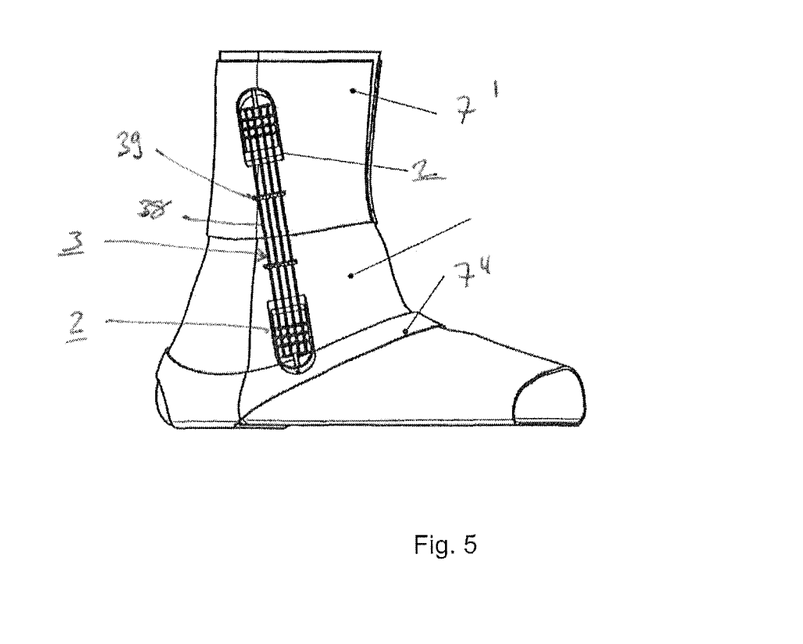
FIG. 5 shows schematically the orthopedic device of FIG. 3 in an arrangement for the adaptive limitation of movement of an ankle joint.

FIG. 5 shows the orthopedic device 1 of FIG. 4 in an arrangement for stabilizing an ankle joint. Thereby, the receptacles 2 are attached to the holding devices 7' and 7" as shown in FIG. 3.

As applicable, all single features that are shown in the single embodiments can be combined and/or exchanged with each other without departing from the scope of the invention.

REFERENCE SIGNS

1 Device
2 Receptacle
20 Inner surface
21 Opening
3 Pull-out body
30 First surface
31 Second surface
32', 32" Lateral surface
33 Structure
4 Shear thickening fluid
5 Reset means 6 Sealing
7', 7" Holding device
S Clearance
S' Clearance
S" Clearance

The invention claimed is:

1. An orthopedic device for the limitation of the movement of a joint disposed between a first body portion and a second body portion, comprising:
a plurality of substantially flat and polygonal receptacles each comprising a plurality of inner lateral surfaces;
a pull-out body that is movable relative to each receptacle; wherein each receptacle comprises a volume filled with shear thickening fluid that is provided between the plurality of inner lateral surfaces of the receptacle and a plurality of outer lateral surfaces of the pull-out body,
wherein the volume filled with shear thickening fluid is defined by a gap between the plurality of inner lateral surfaces of each receptacle and the plurality of outer lateral surfaces of the pull-out body; and
wherein the plurality of the receptacles comprise a first receptacle configured to be fixable to a first body portion at a first end of the pull-out body and a second receptacle configured to be fixable to a second body portion at a second end of the pull-out body.

2. The orthopedic device of claim 1, wherein the pull-out body is linearly movable in the receptacles.

3. The orthopedic device of claim 1, wherein the gap has a clearance of 0.1 to 100 mm, 0.1 to 50 mm, 0.1 to 15 mm, or 0.1 to 5 mm.

4. The orthopedic device of claim 1, wherein: the gap has a first clearance between the inner surface of each receptacle and first and second surfaces of the pull-out body; the gap has a second clearance between the inner surface of each receptacle and lateral surfaces of the pull-out body; and the first and second clearances differ from each other in size.

5. The orthopedic device of claim 1, wherein each receptacle further comprises an elastic synthetic material, a spring, two permanent magnets, a sealing disposed between the receptacle and the pull out body, and/or a sealing bellows configured to reset the pull-out body into a starting position inside the receptacle.

6. The orthopedic device of claim 1, wherein at least a portion of a surface of the pull-out body and/or the receptacles are in communication with the shear thickening fluid are disposed vertically to a normal of the pull-out direction, and comprise a structure.

7. The orthopedic device of claim 6, wherein the structure comprises shapings, fins, grooves and/or nubs.

8. The orthopedic device of claim 1, wherein the receptacles each provide an opening out of which the pull-out body protrudes.

9. The orthopedic device of claim 1, wherein the receptacles each have a sealing to seal the movement of the pull-out body.

10. The orthopedic device of claim 9, wherein, for each of the receptacles, the a first end of the sealing is connected to the receptacle and a second end is connected to the pull-out body, wherein the sealing is movable like a bellows.

11. The orthopedic device of claim 1, wherein each of the receptacles are made of synthetic material, thermoplastic synthetic material, polypropylene, polyethylene, and/or polyurethane.

12. The orthopedic device of claim 1, wherein each receptacle comprises a holding device mountable to the first or second body portion.

13. The orthopedic device of claim 1, wherein the shear thickening fluid comprises a dispersion of ethylene glycol, silicon dioxide, or silica gel with a particle size of 5 to 1000 nm and surfaces of 30 to 250 m2/g, a solid content of 10 to 80%-by weight, and stabilizers.

14. An orthopedic device for limitation of movement of a joint disposed between a first body portion and a second body portion, comprising:
a substantially flat and polygonal receptacle fixable adjacent the first body portion; and
a pull-out body fixable to the second body portion and movable relative to the receptacle, wherein the receptacle comprises an inner surface including a volume filled with shear thickening fluid is provided between the inner surface of the receptacle and the pull-out body,
wherein the pull-out body comprises a plurality of pull-out rods configured to allow the shear thickening fluid to flow into spaces between the plurality of rods.

15. The orthopedic device of claim 14, wherein the receptacle and/or the pull-out body comprises a holding device mountable to at least one of the body portions.

16. An orthopedic device for the limitation of the movement of a joint disposed between a first body portion and a second body portion, comprising:
a substantially flat and polygonal receptacle fixable adjacent to the first body portion; and
a pull-out body fixable to the second body portion and movable relative to the receptacle; wherein the receptacle comprises a volume filled with shear thickening fluid that is provided between a plurality of inner lateral surfaces of the receptacle and the pull-out body,
wherein the volume filled with shear thickening fluid is defined by a gap between the plurality of inner lateral surfaces of the receptacle and the pull-out body;
wherein the pull-out body consists of separate fiber strands made out of reinforcing fibers configured to allow the shear thickening fluid to flow into spaces between the plurality of separate fiber strands, the reinforcing fibers comprising fibers selected from the group consisting of natural fibers, aramid fibers, glass fibers, carbon fibers, synthetic fibers, and any combination thereof.

17. The orthopedic device of claim 16, wherein a portion of the fiber strands of the pull-out body protrudes out of the receptacle.

18. The orthopedic device of claim 16, wherein the fiber strands are held together by means of cross members.

19. The orthopedic device of claim 16, wherein the fiber strands may be subjected to tension only.

20. The orthopedic device of claim 16, wherein the shear thickening fluid contacts the reinforcing fibers.

* * * * *